(12) United States Patent
Li et al.

(10) Patent No.: US 7,880,003 B2
(45) Date of Patent: Feb. 1, 2011

(54) METHOD FOR MAKING TRIS (8-HYDROXYQUINOLINE) NANO-CRYSTAL

(75) Inventors: Ya-Dong Li, Beijing (CN); Wei Chen Chen, Beijing (CN)

(73) Assignees: Tsinghua University, Beijing (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 695 days.

(21) Appl. No.: 12/002,142

(22) Filed: Dec. 14, 2007

(65) Prior Publication Data

US 2008/0234484 A1 Sep. 25, 2008

(30) Foreign Application Priority Data

Mar. 23, 2007 (CN) .................. 2007 1 0073648

(51) Int. Cl.
*C07D 215/30* (2006.01)
(52) U.S. Cl. .................. 546/7; 977/896; 977/788
(58) Field of Classification Search .................. 546/7; 977/896, 788

See application file for complete search history.

(56) References Cited

U.S. PATENT DOCUMENTS

2005/0037083 A1 2/2005 Brynjelsen et al.
2005/0165120 A1 7/2005 Kumar et al.

OTHER PUBLICATIONS

Chun-Pei Cho, "On heat treatment of nanostructured AlQ3-Structural transformation, field emission and photoluminescence", Tsing Hua University, 2006.
Cheung CH, Djurisic AB, Leung YH, et al., "Tris (8-hydroxyquinoline) aluminium nanowires: a simple synthesis method", Chemical Physics Letters, vol. 394, Issue: 1-3, pp. 203-206, 2004.
Chi-An Wu, "On the growth mechanism and heat treatment of Alq3 nanoparticles", Tsing Hua University, 2004.

*Primary Examiner*—Nizal S Chandrakumar
(74) *Attorney, Agent, or Firm*—Jeffrey T. Knapp

(57) ABSTRACT

A method for making a tris-(8-hydroxyquinoline) aluminum (Alq3) nano-crystals includes the steps of: (a) dissolving Alq3 powders into a solvent to form a solution A; (b) dissolving a surfactant in water to achieve a solution B; (c) uniformly mixing the solution A and the solution B to form a latex C; and (d) removing the solvent from the latex C, and subsequently, subjecting the remaining solute to centrifugal separation to form Alq3 nano-crystals.

10 Claims, 8 Drawing Sheets

METHOD FOR MAKING TRIS (8-HYDROXYQUINOLINE) NANO-CRYSTAL

BACKGROUND

1. Field of the Invention

The invention relates to a method for making tris (8-hydroxyquinoline) aluminum (Alq3), particularly, to a method for making Alq3 nano-crystal.

2. Discussion of Related Art

Tris (8-hydroxyquinoline) aluminum (Alq3) has high thermal stability, good chemical stability, excellent electronic transmission performance and luminescent properties. Due to these and other properties, Alq3 is widely used in a variety of fields, such as organic light-emitting diodes, large-screen displays, field emission films, and fluorescent markings. With the development of nano-science and technology, the synthesis of Alq3 nano-crystals with uniform structure attracted a great deal of attention.

Nowadays, the main synthetical method for preparing the Alq3 nano-crystals is vapor method. A steam-condensed method is used to manufacture Alq3 nano-spheres and Alq3 nano-wires, but crystal nano-spheres are not acquired. An adsorbent-assisted physical-vapor-deposition (PVD) method is used to prepare Alq3 nano-wires. However, the above methods for synthesizing Alq3 nano-crystals are complicated, require special equipment, need higher reaction temperature and consume a tremendous amount of protective gas (some of which is expensive rare gas), and as a result, greatly increase the cost of synthesizing the Alq3 nano-crystals. Therefore, these methods are not ideal for large-scale production. Moreover, the Alq3 nano-crystals manufactured via the above methods are difficult to form a film with compact and homogeneous morphology, and thereby restricting its actual application.

What is needed, therefore, is a simple, low cost, and useful large-scale production method for making Alq3 nano-crystals and for forming a film of Alq3 nano-crystals.

SUMMARY

In one embodiment, a method for making a tris-(8-hydroxyquinoline) aluminum (Alq3) nano-crystals includes the steps of: (a) dissolving Alq3 powders into a solvent to form a solution A; (b) dissolving a surfactant in water to achieve a solution B; (c) uniformly mixing the solution A and the solution B to form a latex C; and (d) removing the solvent from the latex C, and subsequently, subjecting the remained solute to centrifugal separation to form Alq3 nano-crystals.

Other advantages and novel features of the present method for making Alq3 nano-crystals will become more apparent from the following detailed description of present embodiments when taken in conjunction with the accompanying drawings.

BRIEF DESCRIPTION OF THE DRAWINGS

Many aspects of the present method for making Alq3 nano-crystals can be better understood with reference to the following drawings. The components in the drawings are not necessarily to scale, the emphasis instead being placed upon clearly illustrating the principles of the present method for making the Alq3 nano-crystals.

Figure 1:
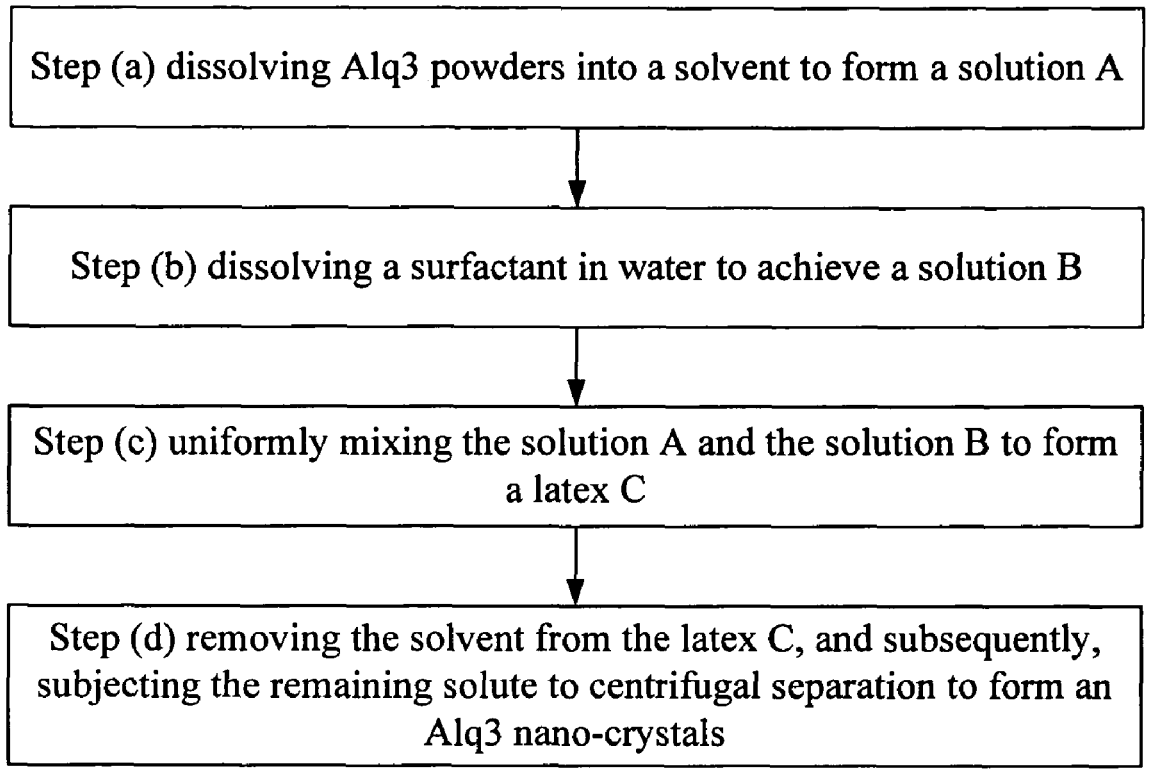
FIG. 1 is a flow chart of a method for making Alq3 nano-crystals in accordance with present embodiments.

Corresponding reference characters indicate corresponding parts throughout the several views. The exemplifications set out herein illustrate at least one preferred embodiment of the present method for making the Alq3 nano-crystals, in at least one form, and such exemplifications are not to be construed as limiting the scope of the invention in any manner.

DETAILED DESCRIPTION OF PREFERRED EMBODIMENTS

Reference will now be made to the drawings to describe, in detail, embodiments of the method for making Alq3 nano-crystals.

Referring to FIG. 1, a method for making a tris-(8-hydroxyquinoline) aluminum (Alq3) nano-crystals includes the steps of: (a) dissolving Alq3 powders into a solvent to form a solution A; (b) dissolving a surfactant in water to achieve a solution B; (c) uniformly mixing the solution A and the solution B to form a latex C; (d) removing the solvent from the latex C, and subsequently, subjecting the remaining solute to centrifugal separation to form an Alq3 nano-crystals.

In step (a), the solvent is, appropriately, an organic solvent. Beneficially, the solvent includes at least one material selected from a group consisting of acetone, N, N-dimethylformamide, chloroform, methylene chloride, and dimethyl sulfoxide. The evaporated solvent can be reused via cooling, collecting, and separating. A concentration of the Alq3 in the solution A is in an approximate range from 6.0 mg/ml (milligram/milliliter) to 10.0 mg/ml.

In step (b), the surfactant includes at least one material selected from a group consisting of polyvinylpyrrolidone (PVP), cetyltrimethylammonium bromide (CTAB), sodium dodecyl sulfate (SDS), and sodium dodecyl benzene sulfonate (SDBS). A concentration of the surfactant in the solution B is in the approximate range from 1.5 mg/ml to 4.0 mg/ml.

In step (c), the solutions A and B are uniformly mixed together by agitating or ultrasonically vibrating vigorously the mixture. In step (d), the solvent is removed at a temperature in an approximate range from 40° C. to 90° C. via agitating to vaporize, or decompressed distilling for about 2 h~8 h, and subsequently, subjecting to centrifugal separation to form Alq3 nano-crystals. The Alq3 nano-crystals are, beneficially, dispersed into water to avoid the aggregation thereof.

The Alq3 nano-crystals synthesized by the method can be nano-rods or nano-spheres. Diameters of the Alq3 nano-rods are in the approximate range from 300 nanometers to 1000 nanometers. Lengths of the Alq3 nano-rods are in the approximate range from 1 micrometer to 10 micrometers. Diameters of the Alq3 nano-spheres are in the approximate range from 50 nanometers to 300 nanometers. Morphology of the Alq3 nano-crystals can be controlled via species and amount of the surfactant, e.g., Alq3 nano-rods can be prepared via adopting CTAB as surfactant, Alq3 nano-spheres can be prepared via adopting SDS as surfactant, the more surfactant used, the bigger the ratio of length to diameter of the nano-rods and the smaller the diameter of the Alq3 nano-spheres, and correspondingly, the less surfactant used, the smaller the ratio of the length to diameter of the nano-rods and the bigger the diameter of the Alq3 nano-spheres. The Alq3 nano-crystals manufactured by the present method have a good dispersion property.

The following examples are provided by way of illustration to show how the present Alq3 nano-crystals can be prepared, and should not be construed as limiting the invention in any way.

EXAMPLE (1)

Figure 2:
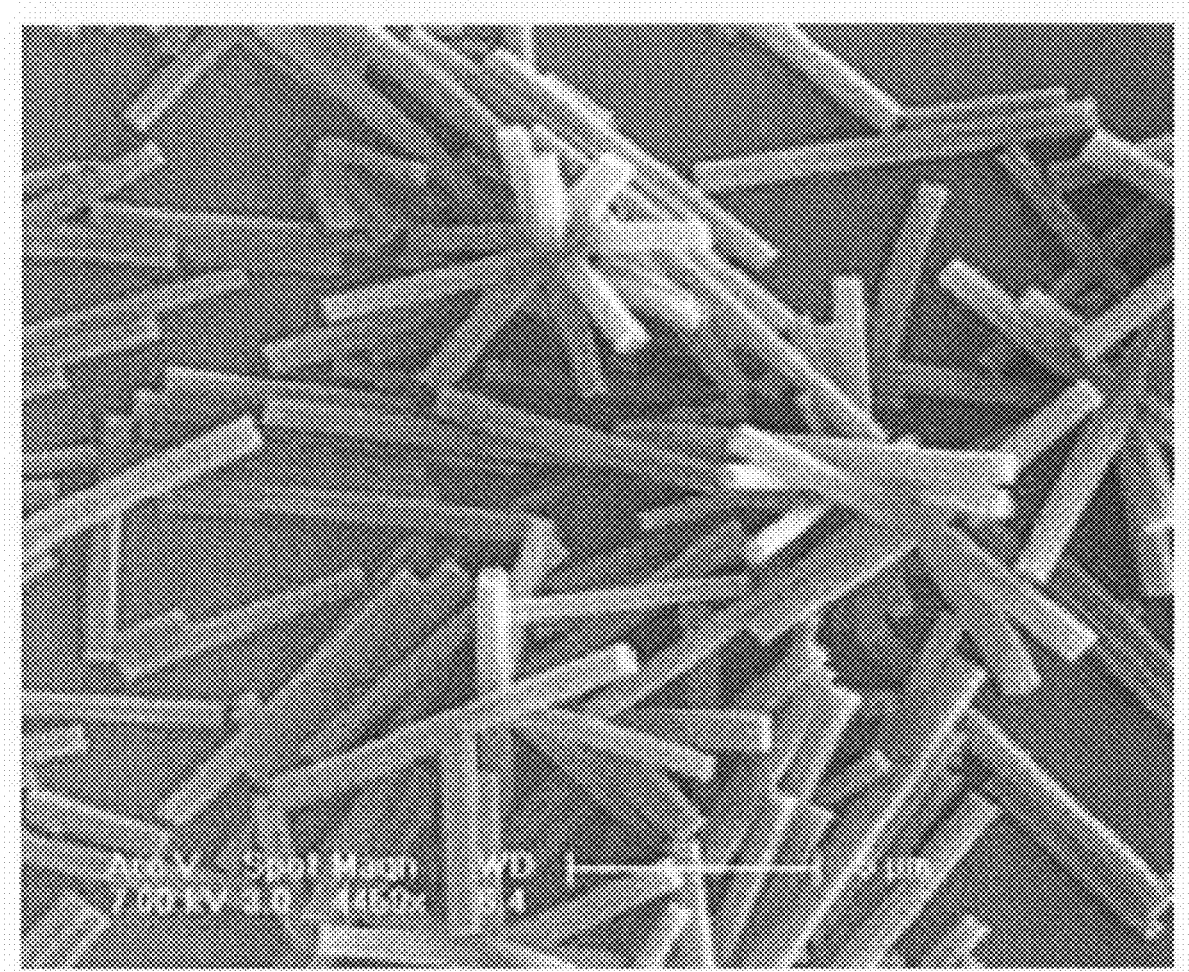
FIG. 2 shows a Scanning Electron Microscope (SEM) image of Alq3 nano-rods in accordance with a first embodiment.
Figure 3:
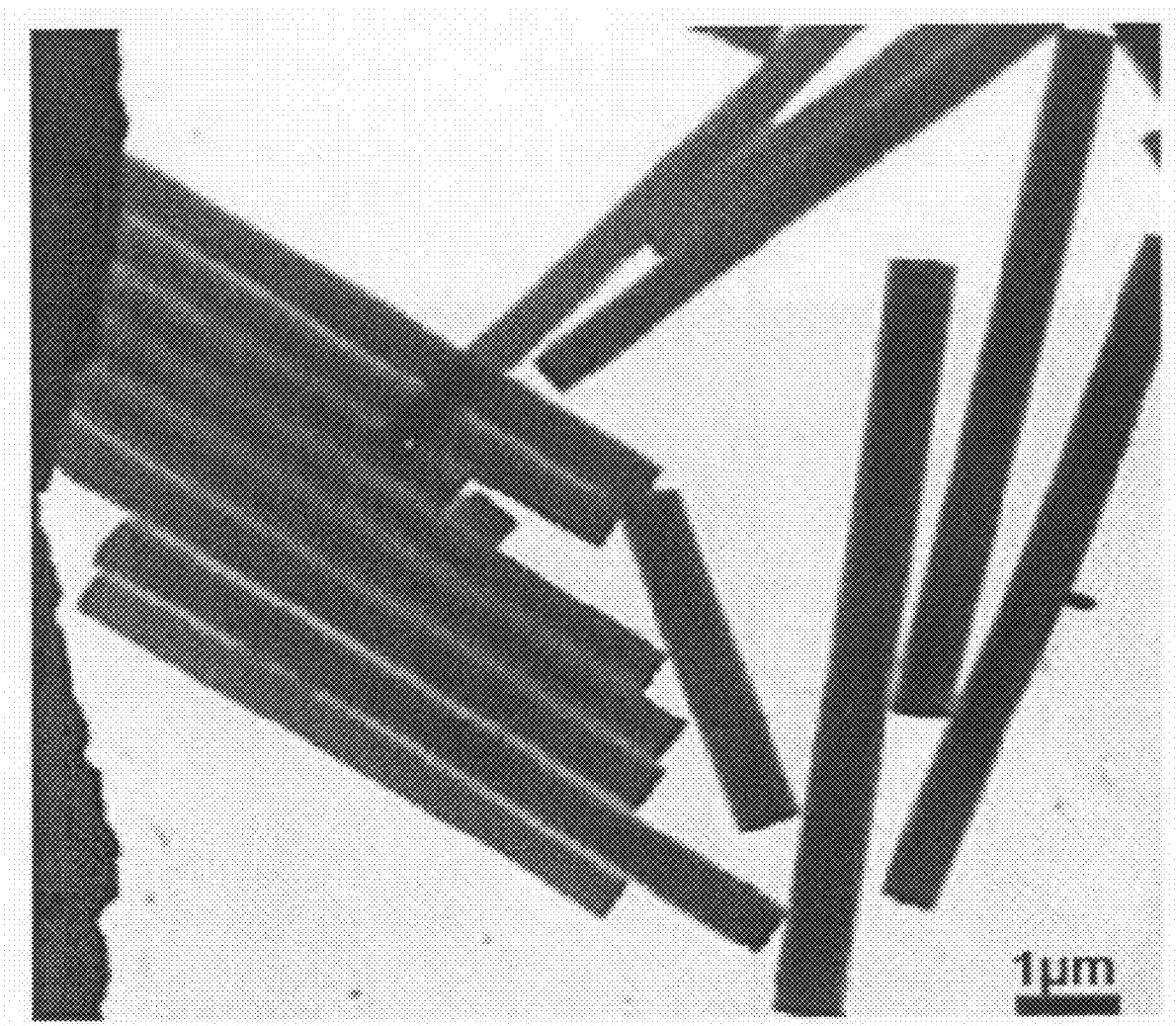
FIG. 3 shows a Transmission Electron Microscope (TEM) image of the Alq3 nano-rods in accordance with a first embodiment.
Figure 4:
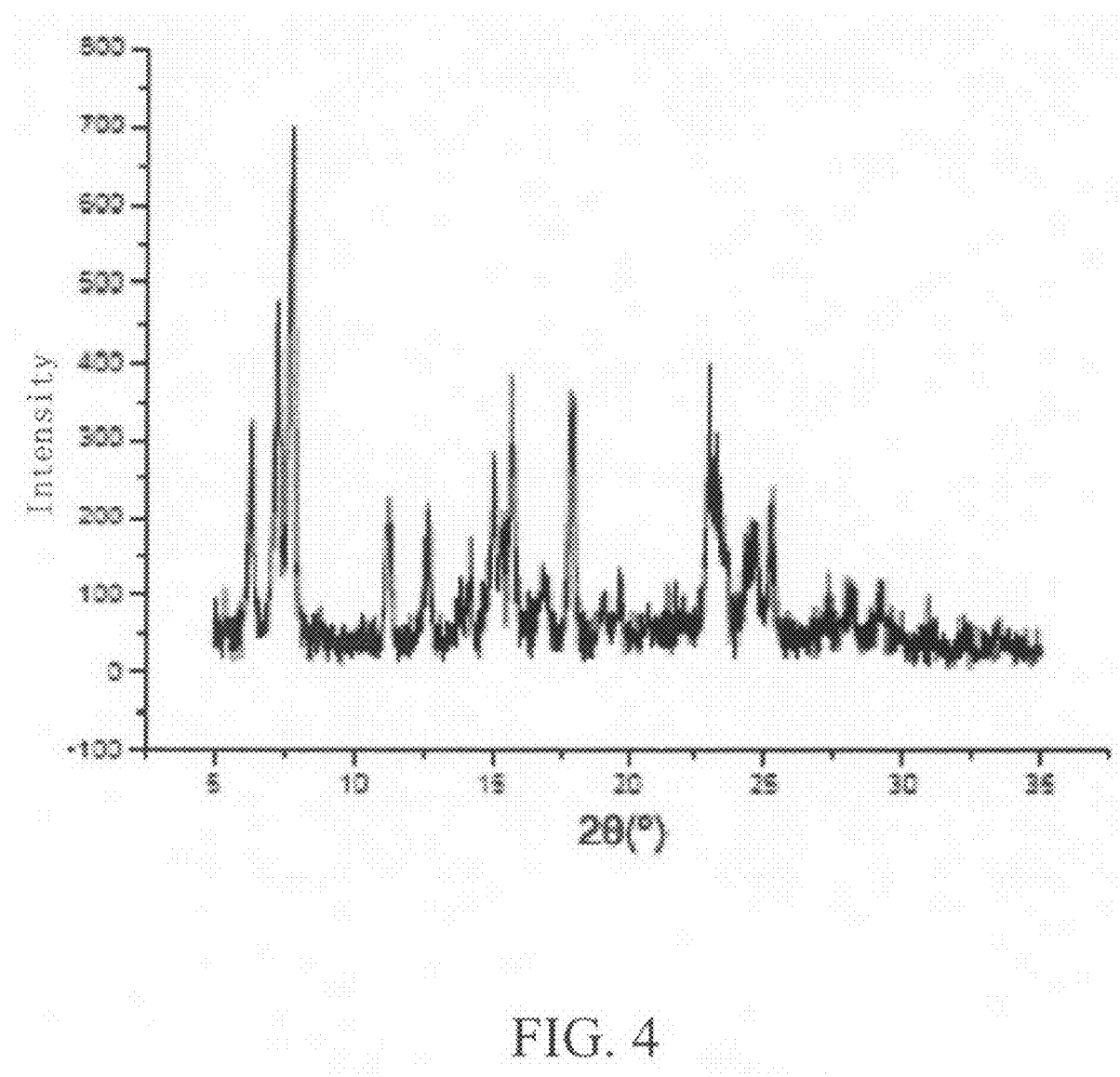
FIG. 4 shows a powder X-ray Diffraction (XRD) image of the Alq3 nano-rods in accordance with a first embodiment.

Firstly, about 8 mg of Alq3 powder is dissolved into 1 ml of chloroform ($CHCl_3$) to form a solution A; secondly, about 30 mg (milligram) of CTBA is dissolved into water to form a solution B; thirdly, the solution A and the solution B are mixed uniformly together via ultrasonically vibrating with a power of 120 w to form a latex C; fourthly, the latex is agitated to vaporize at a temperature of 60° C. for about 4 hours to remove the chloroform and subsequently subjected to centrifugal separation to form Alq3 nano-rods. Diameters of the Alq3 nano-rods manufactured via the first embodiment are about 650 nanometers. Lengths thereof are in the approximate range from 5 micrometers to 10 micrometers. Finally, the nano-rods are dispersed into water to avoid agglomeration. A Scanning Electron Microscope (SEM) image and a Transmission Electron Microscope (TEM) image of the nano-rods are shown in FIG. 2 and FIG. 3 respectively. A powder X-ray Diffraction (XRD) image is shown in FIG. 4. A crystal phase of the Alq3 nano-crystals is, as can be seen in FIG. 4, α phase.

EXAMPLE (2)

Figure 5:
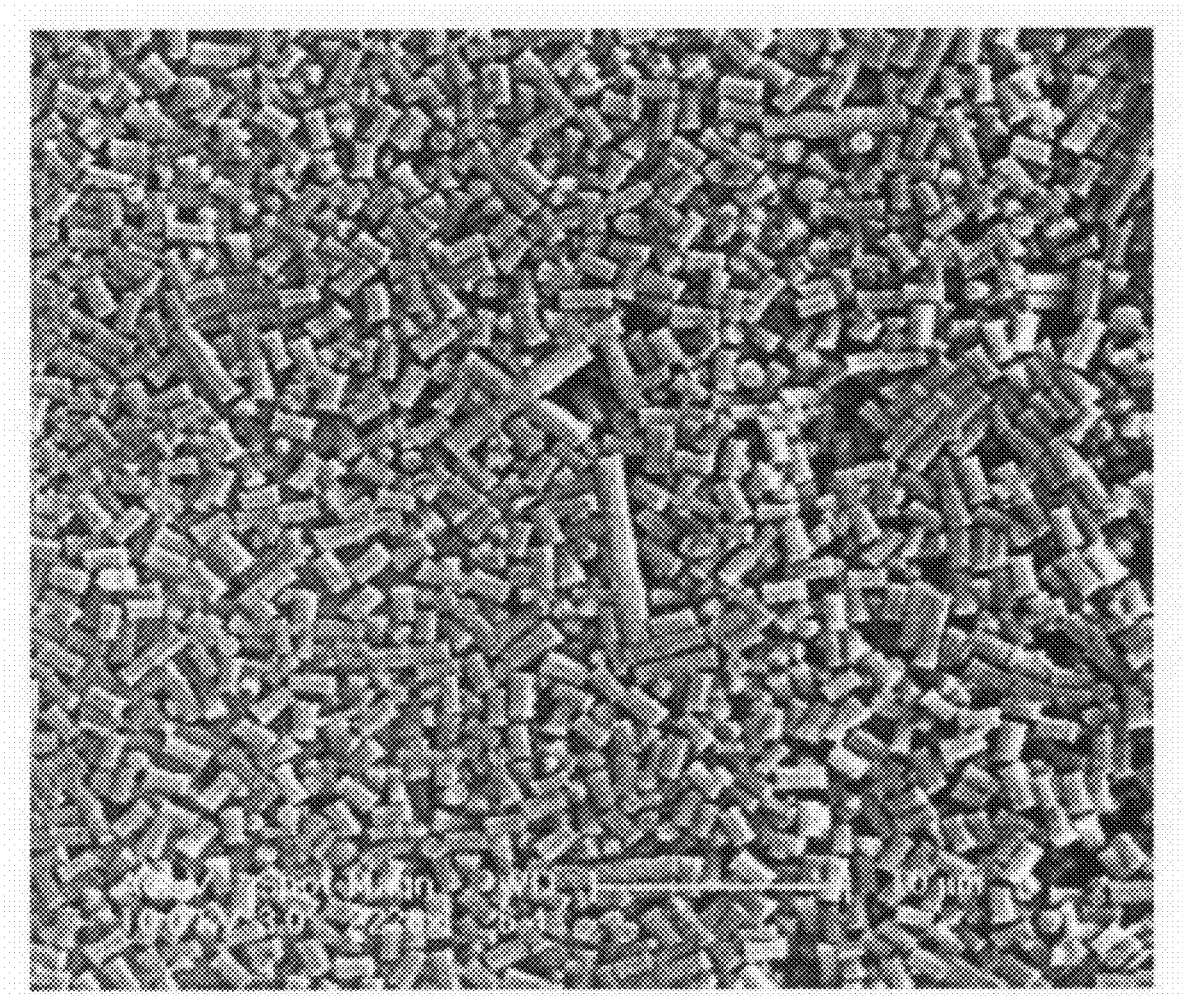
FIG. 5 shows a Scanning Electron Microscope (SEM) image of Alq3 nano-rods in accordance with a second embodiment.

Firstly, about 20 mg of Alq3 powder is dissolved into 2 ml of chloroform ($CHCl_3$) to form a solution A; secondly, about 50 mg of CTBA is dissolved into water of about 20 ml to form a solution B; thirdly, the solution A and the solution B are mixed uniformly together via ultrasonically vibrating with a power of 120 w to form a latex C; fourthly, the latex is agitated to vaporize at a temperature of 60° C. for about 4 hours to remove the chloroform and water, and subsequently subjected to centrifugal separation to form Alq3 nano-rods. Diameters of the Alq3 nano-rods manufactured via the second embodiment are about 900 nanometers. Lengths thereof are in the approximate range from 1.5 micrometers to 2 micrometers. Finally, the nano-rods are dispersed into water to avoid agglomeration. A Scanning Electron Microscope (SEM) image of the nano-rods is shown in FIG. 5.

EXAMPLE (3)

Figure 6:
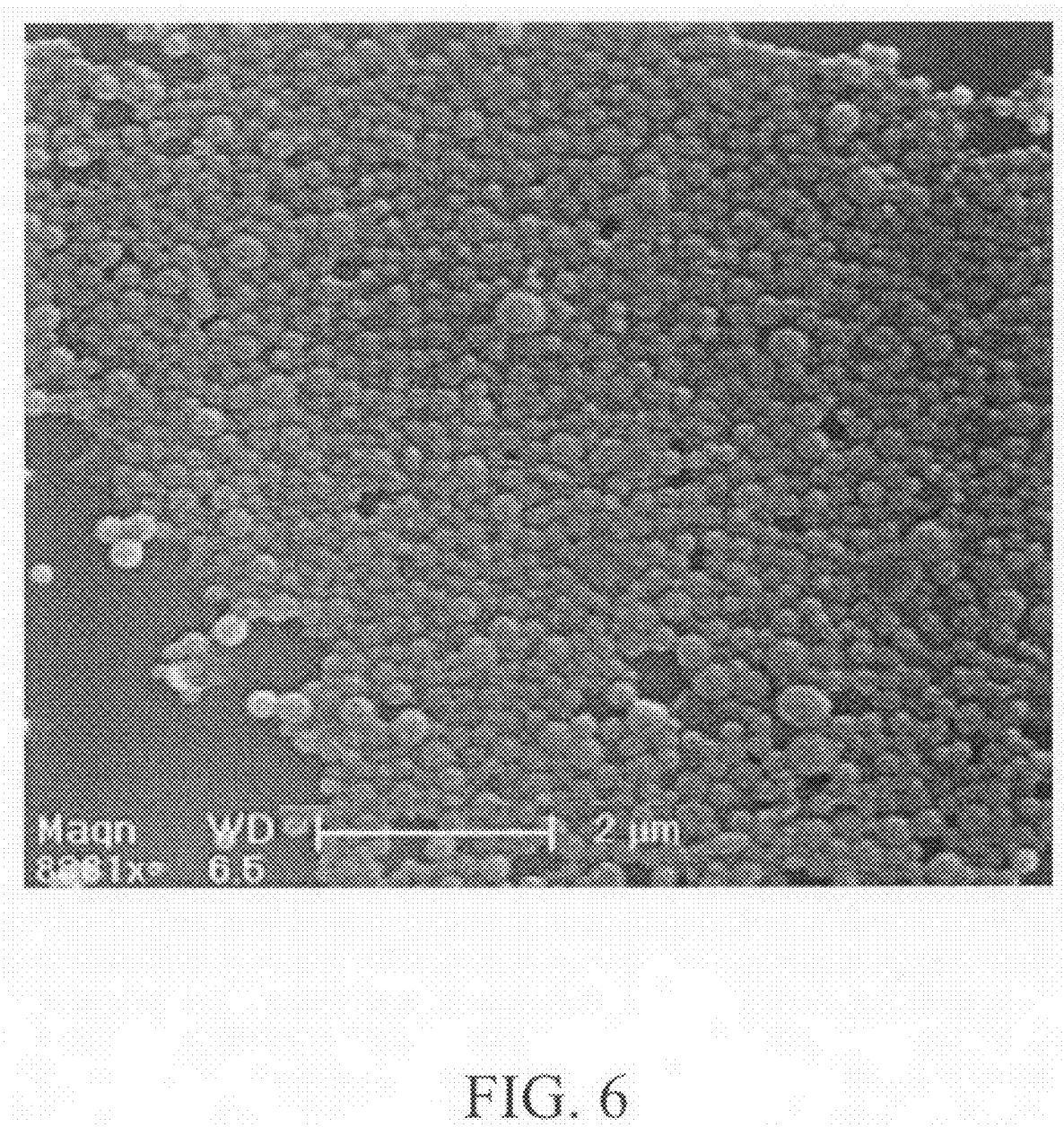
FIG. 6 shows a Scanning Electron Microscope (SEM) image of Alq3 nano-spheres in accordance with a third embodiment.
Figure 7:
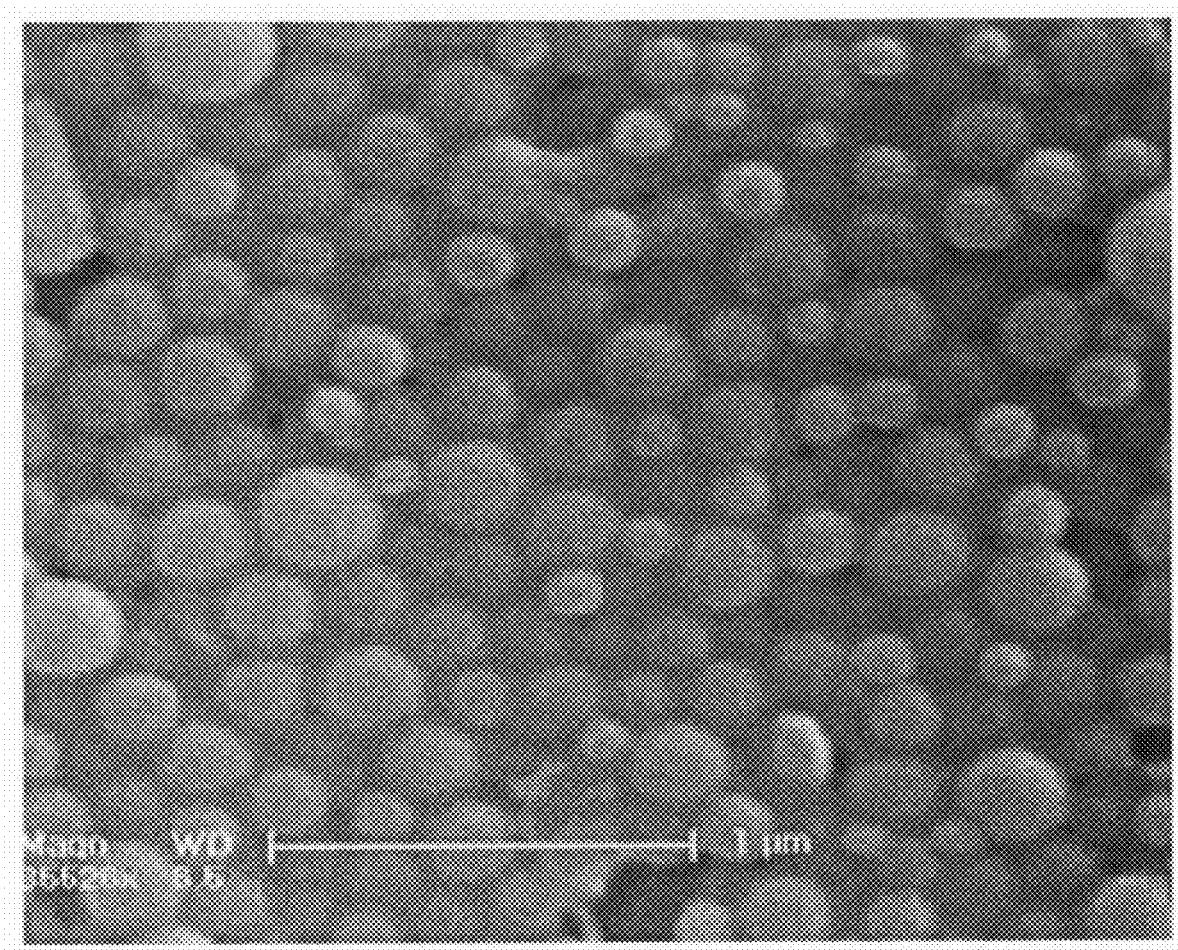
FIG. 7 shows a magnified image of FIG. 6.
Figure 8:
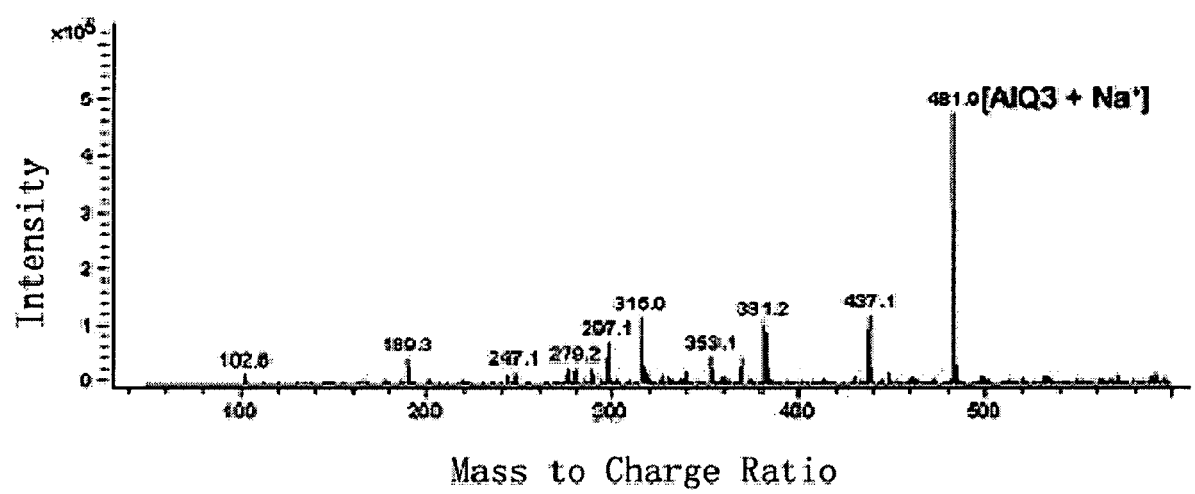
FIG. 8 shows a mass spectrum image of the Alq3 nano-spheres in accordance with a third embodiment.

Firstly, about 8 mg of Alq3 powder is dissolved into 1 ml of chloroform ($CHCl_3$) to form a solution A; secondly, about 60 mg of SDS is dissolved into water of about 16 ml to form a solution B; thirdly, the solution A and the solution B are mixed uniformly together via ultrasonically vibrating with a power of 120 w to form a latex C; fourthly, the latex is agitated to vaporize at a temperature of 60° C. for about 4 hours to remove the chloroform, and subsequently subjected to centrifugal separation to form Alq3 nano-spheres. Diameters of the Alq3 nano-spheres manufactured are in the approximate range from 100 nanometers to 270 nanometers. Finally, the nano-spheres are dispersed into water to avoid agglomeration. Scanning Electron Microscope (SEM) images of the nano-spheres are shown in FIG. 6 and FIG. 7 respectively. A mass spectrum of the Alq3 nano-spheres is shown in FIG. 8. A component of the nano-spheres is, as can be seen in FIG. 8, Alq3.

The present methods for making the tris (8-hydroxyquinoline) aluminum (Alq3) nano-crystals have the following virtues: firstly, since the methods are simple and without need of special equipment, a lot of energy and money can be saved; secondly, on account of the organic solvent evaporated during the manufactured process can be reused after cooling, collecting, and separating, a large amount of raw material can be saved; thirdly, the Alq3 nano-crystals prepared via the aforementioned embodiments are easy to disperse into water to form an Alq3 colloid, and the Alq3 colloid can be spun coated to a material to form a uniform and compact film, and therefore avoid the problems of high-temperature and energy waste in the conventional vacuum evaporation method. So the Alq3 nano-crystals manufactured via the embodiments are useful into large-scale production.

Finally, it is to be understood that the above-described embodiments are intended to illustrate rather than limit the invention. Variations may be made to the embodiments without departing from the spirit of the invention as claimed. The above-described embodiments illustrate the scope of the invention but do not restrict the scope of the invention.

What is claimed is:

1. A method for making Alq3 nano-crystals, comprising the steps of:
   (a) dissolving Alq3 powders into a solvent to form a solution A;
   (b) dissolving a surfactant in water to achieve a solution B;
   (a) uniformly mixing the solution A and the solution B to form a latex C;
   (d) removing the solvent from the latex C, and subsequently, subjecting the remaining solute to centrifugal separation to form Alq3 nano-crystals.

2. The method as claimed in claim 1, wherein in step (a), a concentration of the Alq3 in the solution A is in the approximate range from 6.0 mg/ml to 10.0 mg/ml.

3. The method as claimed in claim 1, wherein in step (a), the solvent includes at least one material selected from a group consisting of acetone, N,N-dimethylformamide, chloroform, methylene chloride, and dimethyl sulfoxide.

4. The method as claimed in claim 1, wherein in step (b), a concentration of the surfactant in the solution B is in the approximate range from 1.5 mg/ml to 4.0 mg/ml.

5. The method as claimed in claim 1, wherein in step (b), the surfactant comprises at least one material selected from a group consisting of polyvinylpyrrolidone (PVP), cetyltrimethylammonium bromide (CTAB), sodium dodecyl sulfate (SDS), and sodium dodecyl benzene sulfonate (SDBS).

6. The method as claimed in claim 1, wherein in step (c), the solution A and B are uniformly mixed together via agitating or vigorously ultrasonically vibrating the mixture.

7. The method as claimed in claim 1, wherein in step (d), the solvent is removed at a temperature in the appropriate range from 40° C. to 90° C. via agitating to vaporize or decompressed distilling for about 2~8 hours.

8. The method as claimed in claim 1, wherein the Alq3 nano-crystals are nano-rods with a diameter thereof in the approximate range from 300 nanometers to 1000 nanometers.

9. The method as claimed in claim 1, wherein the Alq3 nano-crystals are nano-rods with a length thereof in the approximate range from 1 micrometer to 10 micrometers.

10. The method as claimed in claim 1, wherein the Alq3 nano-crystals are nano-spheres with a diameter thereof in the approximate range from 50 nanometers to 300 nanometers.

* * * * *

UNITED STATES PATENT AND TRADEMARK OFFICE
CERTIFICATE OF CORRECTION

PATENT NO. : 7,880,003 B2  
APPLICATION NO. : 12/002142  
DATED : February 1, 2011  
INVENTOR(S) : Ya-Dong Li and Wei Chen Page 1 of 1

It is certified that error appears in the above-identified patent and that said Letters Patent is hereby corrected as shown below:

Title page item (75) "Inventors" should read as follows:

(75) Inventors: Ya-Dong Li, Beijing (CN); Wei Chen, Beijing (CN).

Signed and Sealed this
Twelfth Day of July, 2011

David J. Kappos
*Director of the United States Patent and Trademark Office*